(12) United States Patent
Zhu

(10) Patent No.: US 9,980,517 B2
(45) Date of Patent: May 29, 2018

(54) TOP REFILLABLE ELECTRONIC CIGARETTES

(71) Applicant: Xiaochun Zhu, Shenzhen (CN)

(72) Inventor: Xiaochun Zhu, Shenzhen (CN)

( * ) Notice: Subject to any disclaimer, the term of this patent is extended or adjusted under 35 U.S.C. 154(b) by 0 days. days.

(21) Appl. No.: 14/759,737

(22) PCT Filed: Jun. 19, 2015

(86) PCT No.: PCT/CN2015/081979
§ 371 (c)(1),
(2) Date: Jul. 8, 2015

(87) PCT Pub. No.: WO2016/169119
PCT Pub. Date: Oct. 27, 2016

(65) Prior Publication Data
US 2018/0027874 A1    Feb. 1, 2018

Related U.S. Application Data

(63) Continuation-in-part of application No. PCT/CN2014/093836, filed on Dec. 15, 2014.

(30) Foreign Application Priority Data

Apr. 20, 2015 (CN) .......................... 2015 2 0240929

(51) Int. Cl.
*A24F 47/00* (2006.01)
*F22B 1/28* (2006.01)
*H05B 3/03* (2006.01)

(52) U.S. Cl.
CPC ............ *A24F 47/008* (2013.01); *F22B 1/284* (2013.01); *H05B 3/03* (2013.01)

(58) Field of Classification Search
CPC .................................................... A24F 47/008
See application file for complete search history.

(56) References Cited

U.S. PATENT DOCUMENTS 3,705,785 A  *  12/1972  Goto ....................... F23Q 2/163
                                                                      141/18
4,223,808 A  *   9/1980  Williams ........... B65D 83/0038
                                                                    222/327

(Continued)

FOREIGN PATENT DOCUMENTS

EP          0845220          3/1998
EP          0845220 A1       6/1998

(Continued)

OTHER PUBLICATIONS

European Search Report for corresponding application EP15178749 filed Jul. 29, 2015; dated Apr. 5, 2016.

*Primary Examiner* — James Harvey
(74) *Attorney, Agent, or Firm* — Ming Jiang; MM IP Services LLC

(57) ABSTRACT

Certain aspects of present invention relate to a top refillable e-cigarette, having movable cylindrical e-cigarette assembly, stationary top connecting assembly, and air adjustment assembly. Stationary top connecting assembly is positioned on top of air adjustment assembly. Movable cylindrical e-cigarette assembly may be slid upwards to open an e-liquid refill port against stationary top connecting assembly so e-liquid is refilled at top. Movable cylindrical electronic cigarette assembly has an e-liquid storage tank inside, and a vaporizer body support threadedly connect to a mouthpiece assembly and a sliding base. Stationary top connecting assembly defining a vapor passage in the center of the stationary top connecting assembly configured to allow vaporized e-liquid from the vaporizer to pass through to the mouthpiece assembly. A vaporizer is positioned inside the stationary top connecting assembly. Air adjustment assembly is configured to allow a user to adjust amount of air intake to the top refillable electronic cigarette.

14 Claims, 10 Drawing Sheets

(56) References Cited

U.S. PATENT DOCUMENTS

| | | | |
|---|---|---|---|
| 9,259,035 B2 * | 2/2016 | Terry | A24F 47/008 |
| 2011/0303231 A1 * | 12/2011 | Li | A24F 47/008 |
| | | | 131/329 |
| 2013/0263869 A1 | 10/2013 | Zhu | |
| 2015/0020826 A1 * | 1/2015 | Liu | A24F 47/008 |
| | | | 131/329 |
| 2015/0150307 A1 * | 6/2015 | Liu | H05B 1/0244 |
| | | | 131/329 |
| 2015/0351451 A1 * | 12/2015 | Kaljura | A24D 3/043 |
| | | | 131/280 |
| 2016/0023227 A1 * | 1/2016 | Scott | B05B 11/0097 |
| | | | 141/2 |
| 2016/0023228 A1 * | 1/2016 | Scott | A45D 34/02 |
| | | | 141/2 |
| 2016/0157522 A1 * | 6/2016 | Zhu | A24F 47/008 |
| | | | 131/329 |
| 2017/0049153 A1 * | 2/2017 | Guo | A24F 47/008 |
| 2018/0027874 A1 * | 2/2018 | Zhu | A24F 47/008 |

FOREIGN PATENT DOCUMENTS

| | | |
|---|---|---|
| WO | 2013020220 | 2/2013 |
| WO | 2013020220 A1 | 2/2013 |
| WO | 2013020220 A4 | 2/2013 |

* cited by examiner

TOP REFILLABLE ELECTRONIC CIGARETTES

CROSS-REFERENCE TO RELATED APPLICATIONS

This application is a continuation in part of a PCT/CN2014/093836, filed with the State Intellectual Property Office of China on Dec. 15, 2014, entitled "VAPORIZER AND ELECTRONIC CIGARETTES HAVING THE VAPORIZER", by Xiaochun ZHU, which itself claims priority of Chinese Patent Application No. 201407512212, filed with the Chinese Patent Office on Dec. 9, 2014, entitled "VAPORIZER AND ELECTRONIC CIGARETTES HAVING THE VAPORIZER", also by Xiaochun ZHU, the disclosures of which are incorporated herein in their entireties by reference.

FIELD

The present invention generally relates to the field of electronic cigarette, and more particularly to a top refillable electronic cigarettes.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

It is well known that smoking cigarette is harmful to smoker's health. The active ingredient in a cigarette is mainly nicotine. During smoking, nicotine, along with tar aerosol droplets produced in the cigarette burning, are breathed into the alveolus and absorbed quickly by the smoker. Once nicotine is absorbed into the blood of the smoker, nicotine then produces its effect on the receptors of the smoker's central nervous system, causing the smoker relax and enjoy an inebriety similar to that produced by an exhilarant.

The electronic cigarette is sometimes referred as electronic vaporing device, personal vaporizer (PV), or electronic nicotine delivery system (ENDS). It is a battery-powered device which simulates tobacco smoking. It generally uses a heating element that vaporizes a liquid solution (e-liquid). Some solutions contain a mixture of nicotine and a variety of flavorings, while others release a flavored vapor without nicotine. Many are designed to simulate smoking experience, such as cigarette smoking or cigar smoking. Some of them are made with similar appearance, while others are made considerably different in appearance.

Conventional electronic cigarettes are made with a mouthpiece assembly, a vaporizer assembly, an electric connecting assembly, and an e-liquid storage assembly. The mouthpiece is installed on top of the e-liquid storage assembly, and the vaporizer assembly is installed inside of the e-liquid storage assembly, and electrically connected to a DC power source through the electric connecting assembly. The mouthpiece assembly is connected to the vaporizer assembly and forms an air flow passage. The e-liquid is stored in the e-liquid storage assembly. The e-liquid flows through a vaporizing chamber of the heating assembly using fiber threads. The e-liquid in the fiber threads is then heated by a heating wire of the heating assembly and therefore vaporized. The vaporized e-liquid goes up to the mouthpiece such that a smoker enjoys the vaporized e-liquid.

However, the vapor flow and the quantity and speed of e-liquid vaporization are not controllable or adjustable to meet the different demands of various electronic cigarette smokers.

Therefore, an unaddressed need exists in the art to address the aforementioned deficiencies and inadequacies.

SUMMARY

Certain aspects of the present invention relate to a top refillable electronic cigarette. In certain embodiments, the top refillable electronic cigarette has a movable cylindrical electronic cigarette assembly, a stationary top connecting assembly, and an air adjustment assembly. The stationary top connecting assembly is positioned on top of the air adjustment assembly. The movable cylindrical electronic cigarette assembly may be slid upwards to open an e-liquid refill port against the stationary top connecting assembly such that e-liquid may be refilled at the top through the e-liquid refill port.

In certain embodiments, the movable cylindrical electronic cigarette assembly has an e-liquid storage tank inside the movable cylindrical electronic cigarette assembly, a vaporizer body support having an upper end thread configured to threadedly connect to a mouthpiece assembly, and a lower end thread configured to threadedly connect to a sliding base. The stationary top connecting assembly defining a vapor passage in the center of the stationary top connecting assembly configured to allow vaporized e-liquid from the vaporizer to pass through to the mouthpiece assembly. A vaporizer is positioned inside the stationary top connecting assembly. The air adjustment assembly is configured to allow a user to adjust the amount of air intake to the electronic cigarette In certain embodiments, the electronic cigarette has: the movable cylindrical electronic cigarette body, a vaporizer, the stationary top connecting assembly, a middle connecting assembly, and an air adjustment assembly. The movable cylindrical electronic cigarette assembly has an e-liquid storage tank inside the movable cylindrical electronic cigarette assembly, a vaporizer body support, and a lower end thread. The vaporizer body support has an upper end thread configured to threadedly connect to a mouthpiece assembly, and a lower end thread configured to threadedly connect to the middle connecting assembly. The vaporizer is disposed inside the movable cylindrical electronic cigarette assembly. The stationary top connecting assembly defines a vapor passage in the center of the stationary top connecting assembly. The vapor passage is configured to allow vaporized e-liquid from the vaporizer to pass through to the mouthpiece assembly. The middle connecting assembly has an outside thread at an upper end configured to threadedly connect to the movable cylindrical electronic cigarette assembly. The air adjustment assembly is used to allow a user to adjust the amount of air intake to the electronic cigarette.

In certain embodiments, the vaporizer includes: a circular vaporizer connector, a e-liquid medium, a heating element, and a vaporizer tube. The circular vaporizer connector has an upper end, and an opposite lower end. The circular vaporizer connector defines a center hollow air passage through the lower end to the upper end. The e-liquid medium is placed on the upper end of the circular vaporizer connector. The e-liquid medium has an inside wall and an outside wall and defines a circular vaporizing chamber. The vaporizing chamber has a lower end connected to the center hollow air passage of the circular vaporizer connector, and an upper end forming a vapor discharge. The heating element is disposed on and in direct contact with the inside wall of the e-liquid medium. The heating element has a first terminal, and a second terminal. The vaporizer tube is disposed on and in contact with the outside wall of the e-liquid medium. The vaporizer tube has a lower end and an opposite, upper end. The vaporizer tube defines certain e-liquid conduit openings. These e-liquid conduit openings are used to allow e-liquid from the e-liquid storage tank outside of the vaporizer to flow into the e-liquid medium. When a user fills the e-liquid storage tank with e-liquid, the e-liquid from the e-liquid storage tank flows to the e-liquid medium through the e-liquid conduit openings, and is vaporized by the heating element when the user connects an electric power supply to the first terminal and the second terminal of the heating element. The heating element has a heating wire, and the heating wire is wound in a spiral shape.

In certain embodiments, the e-liquid medium is made from at least one of: cotton fibers, polypropylene fibers, terylene fibers, nylon fibers; and porous ceramic materials. The vaporizer tube has upper end threads used to connect to a stationary top connecting assembly, and a vaporizer tube sealing ring used to seal the connection with the stationary top connecting assembly. The circular vaporizer connector has lower end threads for connecting to a lower connecting assembly. The lower connecting assembly has an upper inside threaded portion threadedly coupled to the lower end threads of the circular vaporizer connector, and a lower outside threaded portion threadedly coupled to an air adjustment assembly.

In certain embodiments, the air adjustment assembly includes: an air adjustment assembly base, an air adjustment ring, and a sealing ring. The air adjustment assembly base has an upper tubular portion threadedly connected to the lower outside threaded portion of the lower connecting assembly, an air adjustment chamber defined inside of the air adjustment assembly base, and a predetermined number of first air vents. The air adjustment ring positioned outside of the upper tubular portion of the air adjustment assembly base. The air adjustment ring has a predetermined number of second air vents. The sealing ring is used to prevent air leak from the air adjustment assembly. When the user rotates the air adjustment ring around the upper tubular portion of the air adjustment assembly base, and when the locations of the second air vents of the air adjustment ring match the locations of the first air vents, air flow from outside to the air adjustment chamber reaches maximum capacity. When the user further rotates the air adjustment ring around the upper tubular portion, the air flow decreases, and when the locations of the second air vents of the air adjustment ring completely misalign with the locations of the first air vents, the air flow stops.

In certain embodiments, the electronic cigarette further includes an e-liquid storage assembly. The e-liquid storage assembly has: an e-liquid storage top sealing ring, an e-liquid storage bottom sealing ring, a transparent e-liquid storage tube, and the vaporizer body support. The e-liquid storage top sealing ring seals the top of the e-liquid storage assembly. The e-liquid storage bottom sealing ring seals the bottom of the e-liquid storage assembly. The transparent e-liquid storage tube configured to allow the user to measure the remaining e-liquid in the e-liquid storage assembly. The e-liquid storage tank is defined inside of the e-liquid storage assembly vertically between the e-liquid storage bottom sealing ring and the e-liquid storage top sealing ring, and horizontally between the vaporizer tube and the transparent e-liquid storage tube.

In certain embodiments, the mouthpiece assembly has: a mouthpiece, a mouthpiece connector, and a mouthpiece sealing ring. The mouthpiece has a hollow center air passage connected to the vapor passage of the stationary top connecting assembly and provides vaporized e-liquid to the user. The mouthpiece connector has a threaded lower portion threadedly connects to the vaporizer body support. The mouthpiece sealing ring prevents the vaporized e-liquid from leaking through the mouthpiece connector.

In certain embodiments, the electronic cigarette further includes an e-liquid refill sealing element disposed on the stationary top connecting assembly and configured to seal the e-liquid storage tank when the mouthpiece connector is installed, and allow the user to refill the e-liquid into the e-liquid storage tank to the transparent e-liquid storage tube when the mouthpiece connector is removed.

In certain embodiments, the electronic cigarette further includes an electric connector assembly. The electric connector assembly has: an electric connector base, an electrode, and an insulation cover. The electric connector base is attached to the air adjustment assembly and adapted for connecting an electric power supply to the heating element of the vaporizer. The electric connector base has an outer thread configured to electrically connect a first terminal of the electric power supply to the first terminal of the heating element. The electrode is used to electrically connect a second terminal of the electric power supply to the second terminal of the heating element. The insulation cover is positioned between the electric connector base and the electrode to provide insulation between the first and the second terminals of the electric power supply.

In certain embodiments, the heating element has a heating wire, and the heating wire is wound in a spiral shape. The electronic cigarette also includes an electric power switch to allow the user to turn on and off the electronic cigarette.

In certain embodiments, the top refillable electronic cigarette 100 includes an electric power. This power switch allows the user to turn on and off the electronic cigarette. In certain embodiments, the top refillable electronic cigarette 100 includes an electric power adjustment device. This electric power adjustment device allows the user to adjust the electric power to control vaporization of the e-liquid.

These and other aspects of the present invention will become apparent from the following description of the preferred embodiment taken in conjunction with the following drawings, although variations and modifications therein may be effected without departing from the spirit and scope of the novel concepts of the invention.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment. The drawings do not limit the present invention to the specific embodiments disclosed and described herein. The drawings are not necessarily to scale, emphasis instead being placed upon clearly illustrating the principles of the invention, and wherein.

DETAILED DESCRIPTION

Figure 1:
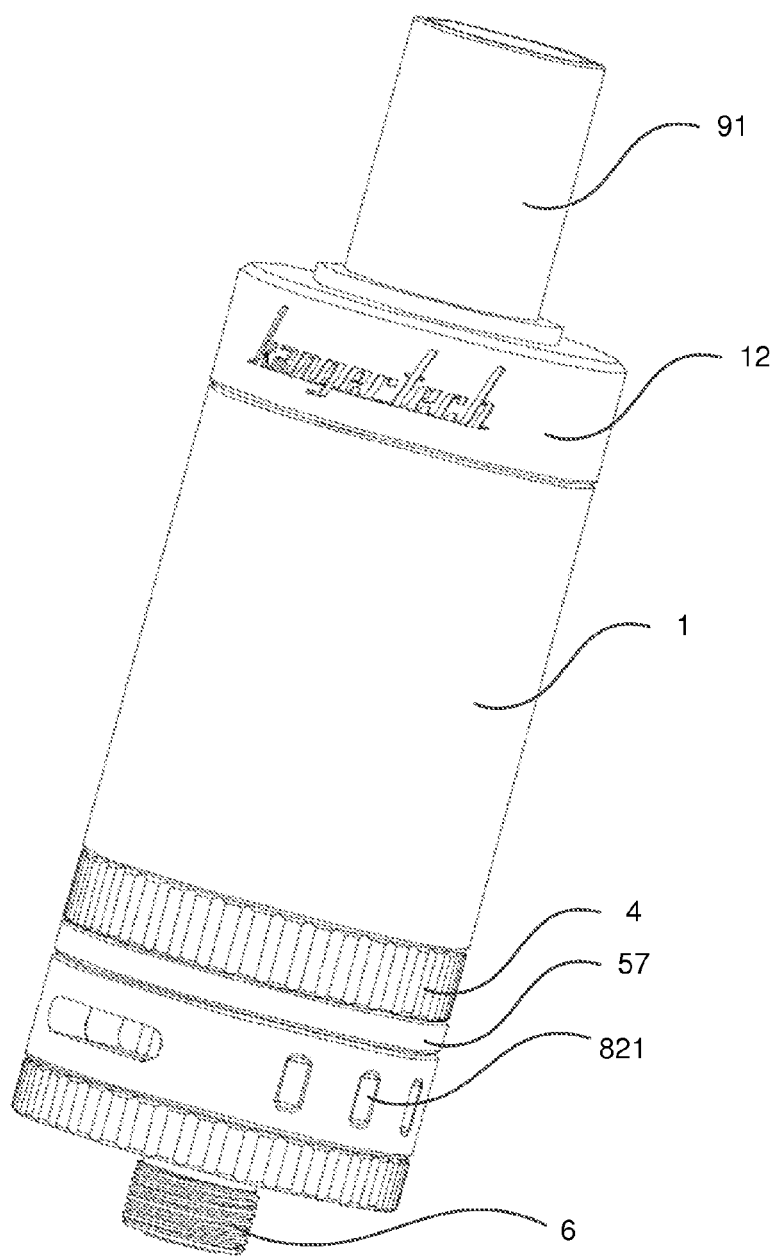
FIG. 1 is a perspective view of a top refillable electronic cigarette according to certain embodiments of the present invention.
Figure 2:
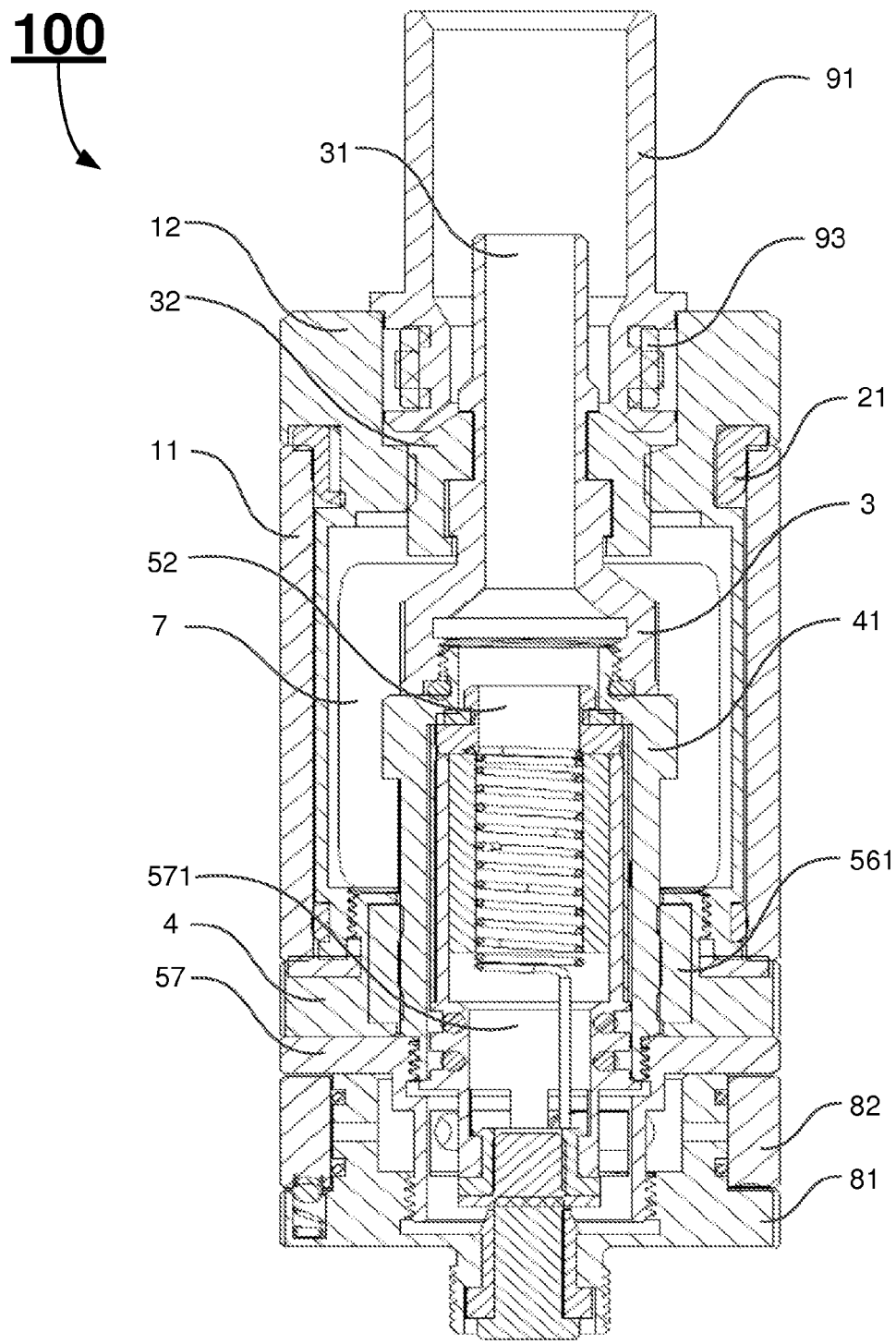
FIG. 2 is a cross-sectional view of the top refillable electronic cigarette according to certain embodiments of the present invention.

The present invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom", "upper" or "top," and "front" or "back" may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximates, meaning that the term "around", "about" or "approximately" can be inferred if not expressly stated.

Many specific details are provided in the following descriptions to make the present invention be fully understood, but the present invention may also be implemented by using other manners different from those described herein, so that the present invention is not limited by the specific embodiments disclosed in the following.

The description will be made as to the embodiments of the present invention in conjunction with the accompanying drawings FIGS. 1 through 10. In accordance with the purposes of this invention, as embodied and broadly described herein, this invention, in one aspect, relates to a vaporizer 5 of electronic cigarettes.

Referring now to FIGS. 1-4, a top refillable electronic cigarette 100 is shown according to certain embodiments of the present invention. The top refillable electronic cigarette 100 has a mouthpiece assembly 9, a movable cylindrical electronic cigarette assembly 1, and an air adjustment assembly 8. The movable cylindrical electronic cigarette assembly 1 has an e-liquid storage support 12. The e-liquid storage support 12 has a top portion having an opening for the mouthpiece assembly 9. At the bottom of the e-liquid storage support 12, a thread is used to threadedly connect to a sliding base 4.

A circular vaporizer connector 57 is positioned on the air adjustment assembly 8 A sliding tube 41 is connected to the air adjustment assembly 8 through a circular vaporizer connector threads 572. A vaporizer 5 is positioned on top of the circular vaporizer connector 57. A stationary top connection assembly 3 threadedly connects to a sliding tube 41. A vapor passage 31 is formed in the center of the stationary top connection assembly 3.

Figure 3:
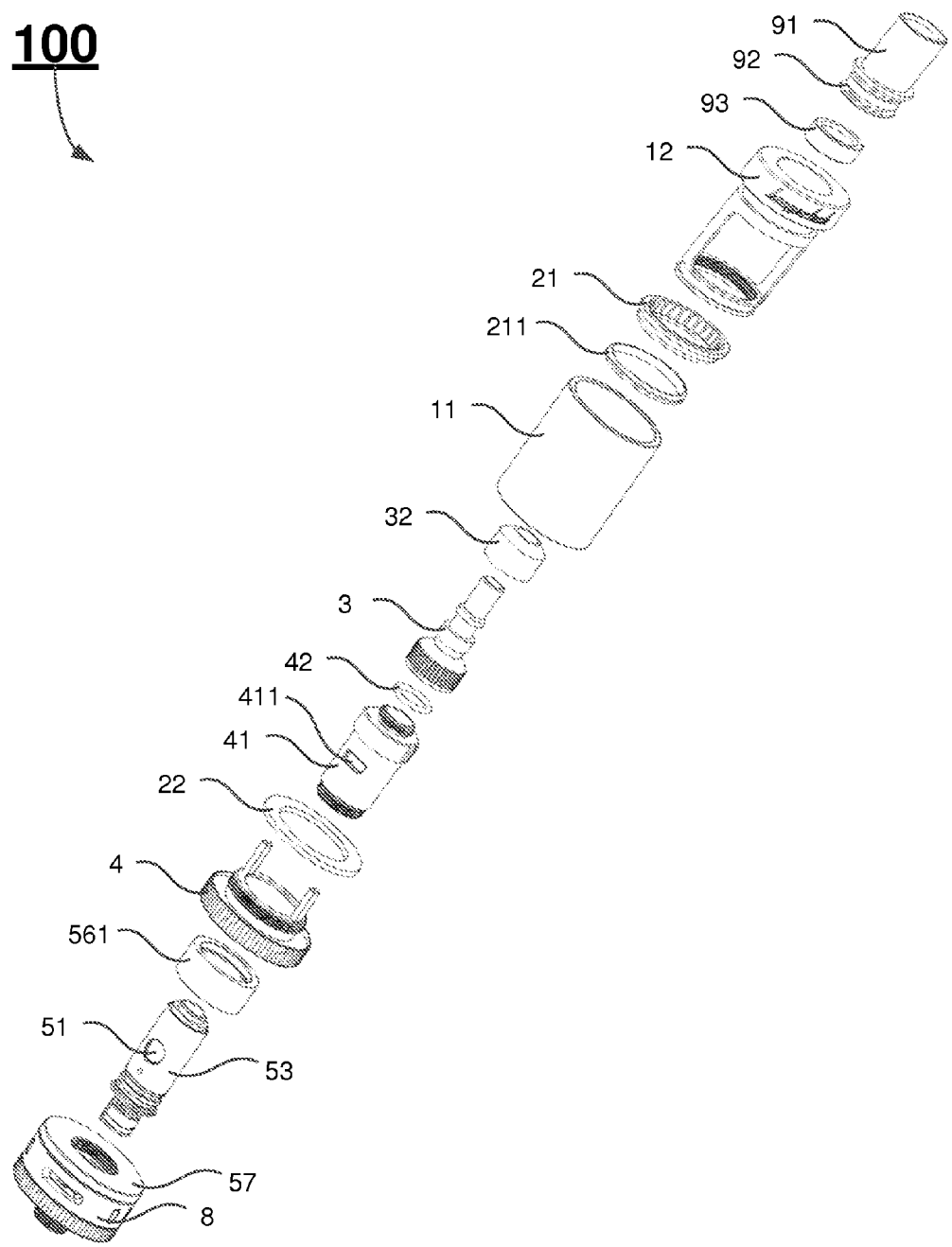
FIG. 3 is a perspective exploded view of the top refillable electronic cigarette according to certain embodiments of the present invention.

Therefore, the stationary portion of the top refillable electronic cigarette 100 includes the stationary top connection assembly 3, an e-liquid refill seal 32, the sliding tube 41, the circular vaporizer connector 57, and the vaporizer 5 inside of the sliding tube 41. A sliding tube sealing ring 42 is used to seal the connection between the stationary top connection assembly 3 and the sliding tube 41, as shown in FIG. 3. The e-liquid refill seal 32 is installed on the top portion of the stationary top connection assembly 3 inside a groove such that the e-liquid refill seal 32 will remain stationary.

The movable portion of the of the top refillable electronic cigarette 100 includes the e-liquid storage support 12, a glass e-liquid storage body 11, the sliding base 4, and a lower connecting assembly sealing ring 561. An e-liquid storage tank top seal 21, and an e-liquid storage tank top sealing ring 211 are used to seal the top portion of an e-liquid storage tank 7 of the top refillable electronic cigarette 100, and an e-liquid storage tank bottom sealing ring 22 is used to seal the bottom portion of the e-liquid storage tank 7 of the top refillable electronic cigarette 100.

Figure 5:
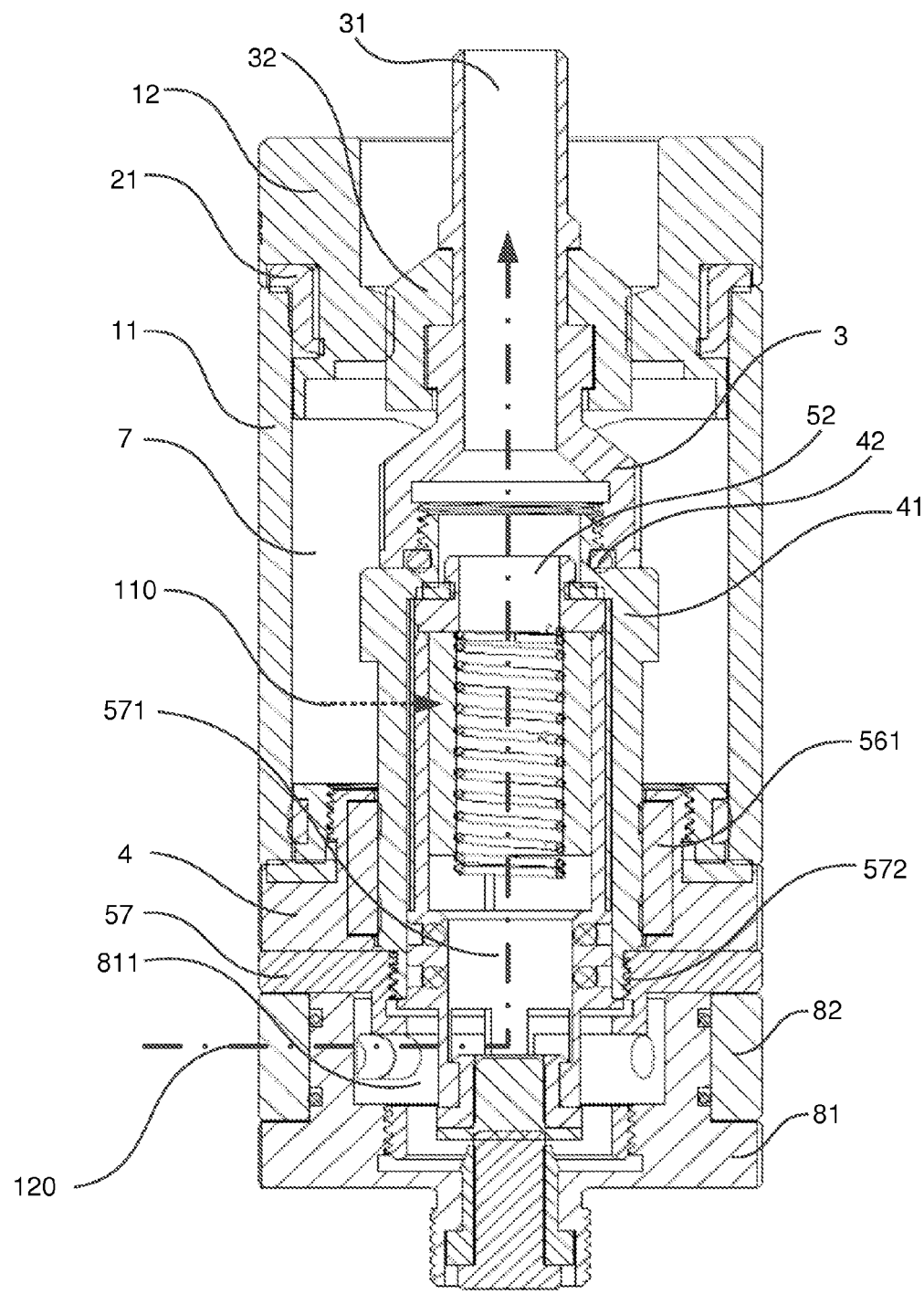
FIG. 5 is a cross sectional view of the top refillable electronic cigarette fully assembled according to certain embodiments of the present invention.

Referring now to FIG. 5, a cross sectional view of the top refillable electronic cigarette 100 is shown according to certain embodiments of the present invention. This is the top refillable electronic cigarette 100 when it is fully assembled, and ready for a user to use. The movable portion of the top refillable electronic cigarette 100 is pushed down the sliding base 4 in full contact with the circular vaporizer connector 57. In this configuration, the e-liquid refill seal 32 is in full contact with an internal wall of the e-liquid storage support 12 such that any e-liquid inside the e-liquid storage tank 7 will not be leaked. A perspective view of this fully assembled top refillable electronic cigarette 100 is shown in FIG. 1 according to certain embodiments of the present invention. When the top refillable electronic cigarette 100 is filled with-liquid in the e-liquid storage tank 7, the e-liquid pass through a pair of sliding tube e-liquid conduit openings 411, a pair of e-liquid conduit openings 51 of the vaporizer 5, to reach an e-liquid medium 55. When the user connects the top refillable electronic cigarette 100 to an electric power source, the electric power source supplies electricity to a heating element 54 and the e-liquid soaked in the e-liquid medium 55 is vaporized and electronic cigarette vapor is formed. An exemplary e-liquid flow 100 is shown in FIG. 5. On the other hand, an air flow 120 for the top refillable electronic cigarette 100 is shown in FIG. 5 as well. The air enters the top refillable electronic cigarette through one or more second air vents 821 on an air adjustment ring 82, one or more first air vents 812 on an air adjustment assembly base 81, an air adjustment chamber 811, and a center hollow air passage 571, a vapor discharge 52, the vapor passage, and finally reach the user through the mouthpiece assembly 9.

Figure 6:
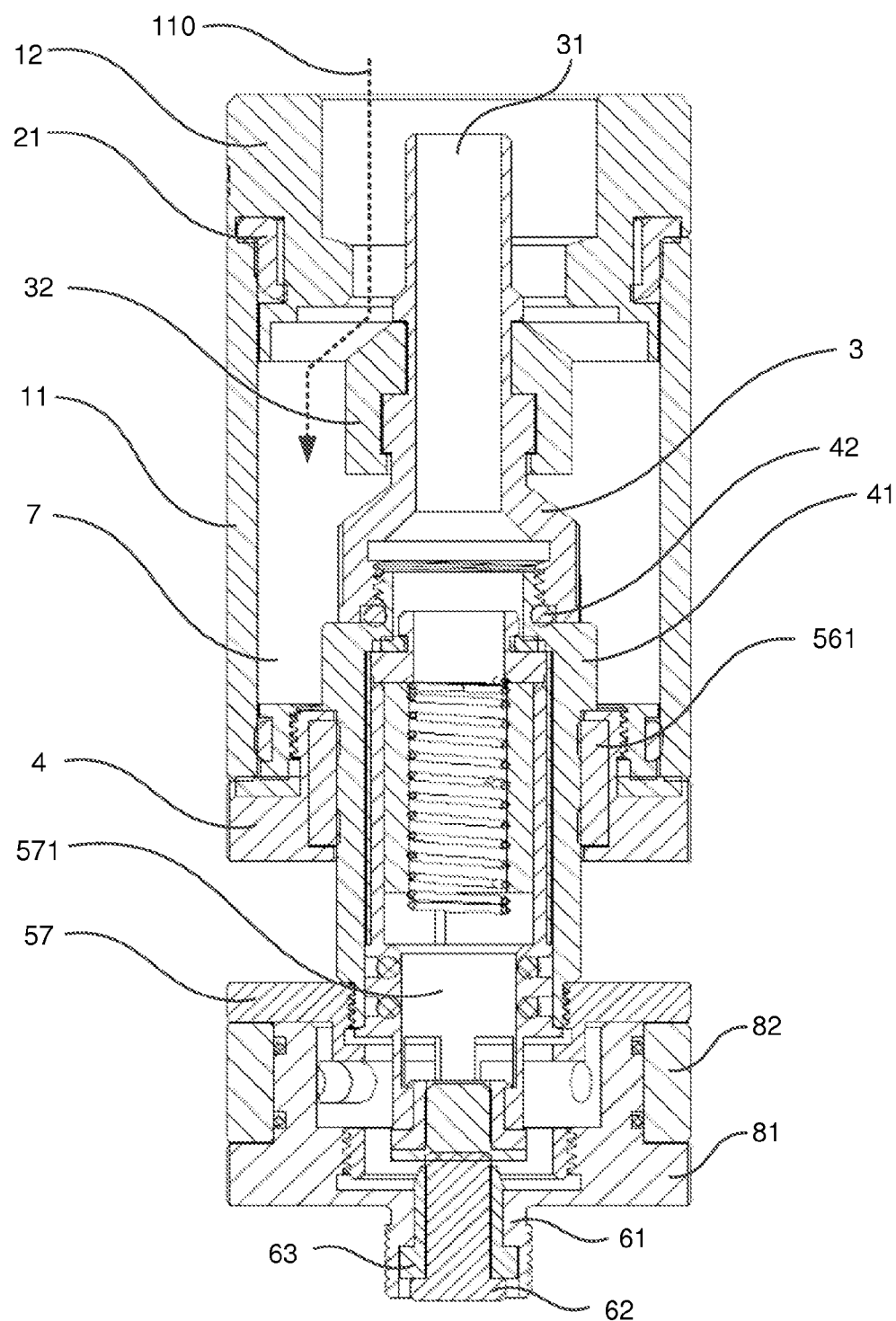
FIG. 6 is a cross sectional view of the top refillable electronic cigarette when a movable cylindrical electronic cigarette assembly is slid upwards for e-liquid refill according to certain embodiments of the present invention.

FIG. 6 is a cross sectional view of the top refillable electronic cigarette when a movable cylindrical electronic cigarette assembly 1 is slid upwards for e-liquid refill according to certain embodiments of the present invention. The user can hold the movable cylindrical electronic cigarette assembly 1 and slide the movable cylindrical electronic cigarette assembly 1 upwards to open an e-liquid refill port. The user can remove the mouthpiece assembly 9 to refill the e-liquid into the e-liquid storage tank 7 through the e-liquid flow 110. Once the e-liquid is refill to an appropriate level, the user can push the movable cylindrical electronic cigarette assembly 1 back down to restore the top refillable electronic cigarette 100 into operation state. When the movable cylindrical electronic cigarette assembly 1 is slid upwards, a lower connecting assembly sealing ring 561 is slid upwards at the same time by the sliding base 4. The lower connecting assembly sealing ring 561 is used to seal the sliding tube e-liquid conduit openings 411 such that the refilled e-liquid will not leaked into the e-liquid medium 55 before the movable cylindrical electronic cigarette assembly 1 is slid down.

Figure 7:
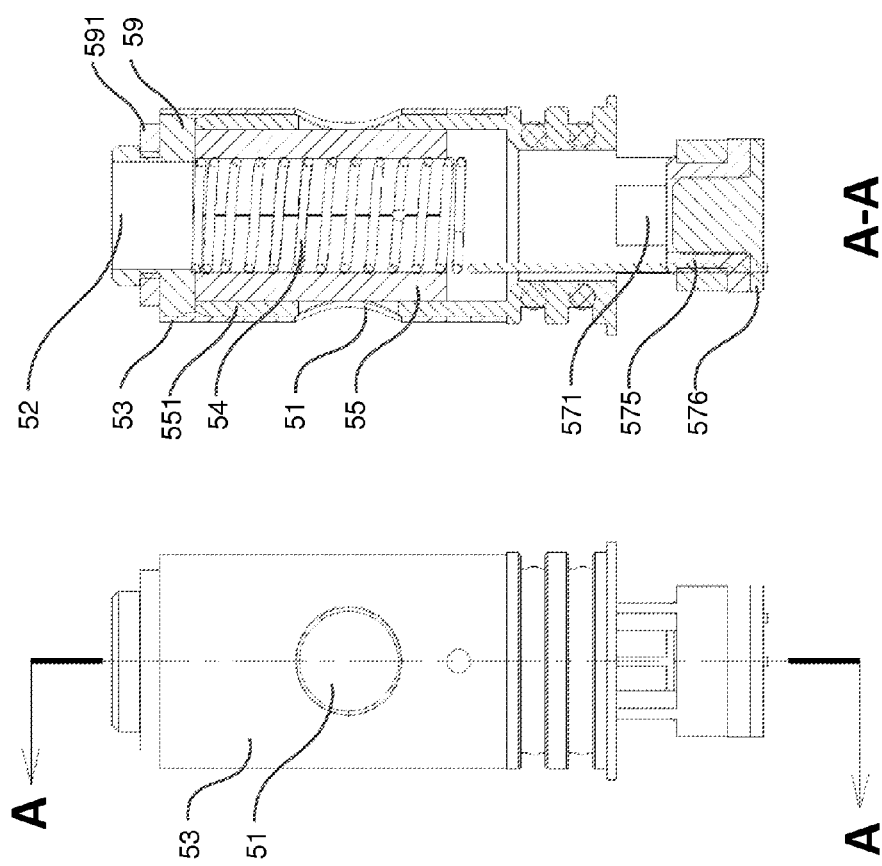
FIG. 7 is a side view and a cross-sectional view of a vaporizer for the top refillable electronic cigarette according to certain embodiments of the present invention.
Figure 8:
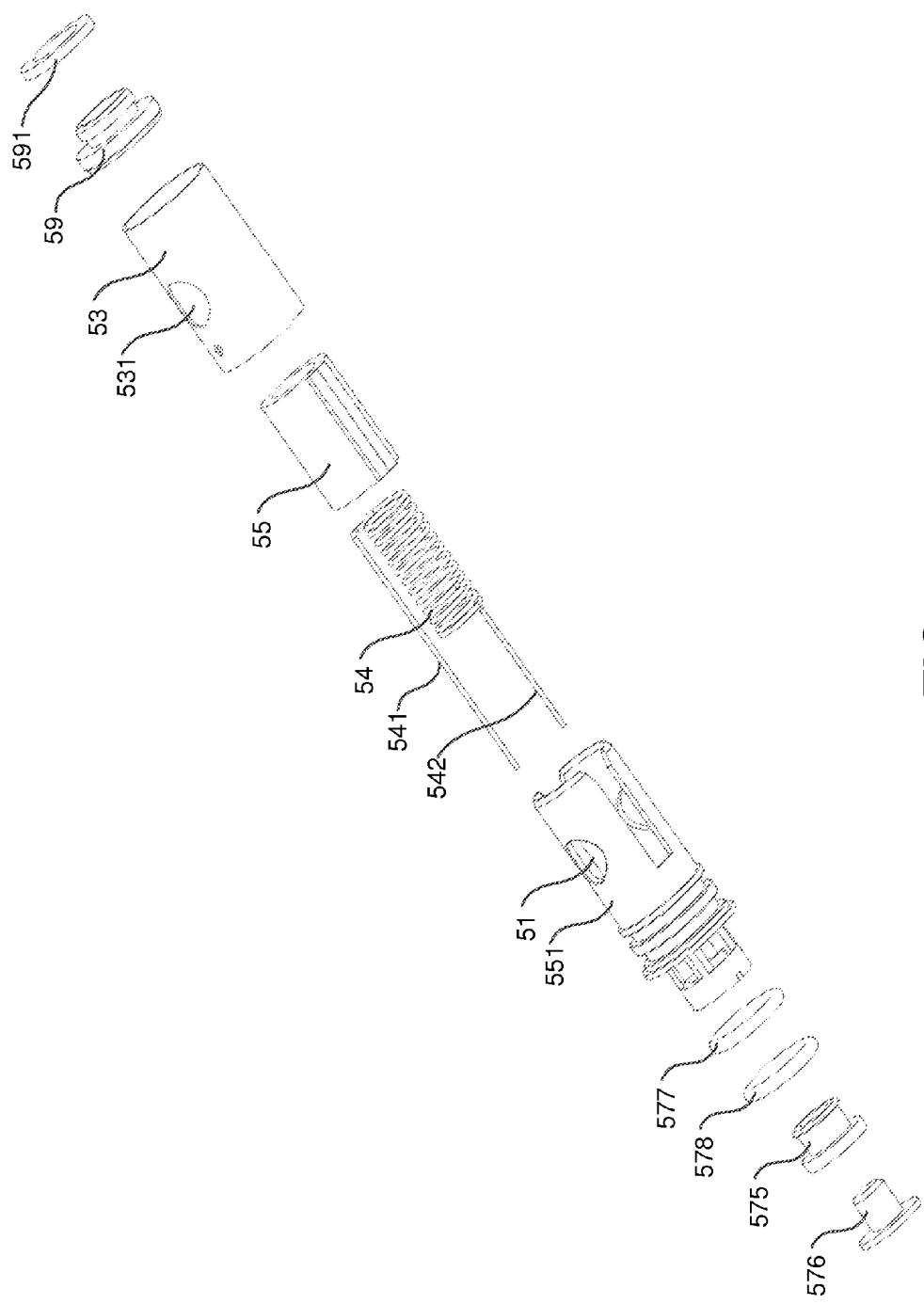
FIG. 8 is a perspective exploded view of the vaporizer for the top refillable electronic cigarette according to certain embodiments of the present invention.

Referring now to FIGS. 7-8, a side view, a cross-sectional view and a perspective exploded view of the vaporizer 5 for the top refillable electronic cigarette 100 are shown according to certain embodiments of the present invention;

In certain embodiments, the vaporizer 5 includes: a circular vaporizer connector 57, a vaporizer top seal 59, a vaporizer top sealing ring 591, an e-liquid medium 55, an e-liquid medium support 551, a heating element 54, and a vaporizer tube 53. The circular vaporizer connector 57 has an upper end, and an opposite lower end. The circular vaporizer connector 57 defines a center hollow air passage 571 through the lower end to the upper end. The e-liquid medium 55 is placed on the upper end of the circular vaporizer connector 57. The e-liquid medium 55 is connected to the e-liquid medium support 551. The e-liquid medium support 551 has a lower end connected to the center hollow air passage 571 of the circular vaporizer connector 57, and an upper end forming a vapor discharge 52 (as shown in FIG. 7). The vaporizer tube 53 has one or more e-liquid conduit openings 531 for passing e-liquid from the e-liquid storage tank 7 to the e-liquid conduit openings 51 of the e-liquid medium support 551 and the e-liquid medium 55.

In certain embodiments, the vaporizer 5 includes a first air adjustment assembly ring 575, a second air adjustment assembly ring 576, a first air adjustment assembly sealing ring 577, and a second air adjustment assembly sealing ring 578. The first air adjustment assembly ring 575, the second air adjustment assembly ring 576, the first air adjustment assembly sealing ring 577, and the second air adjustment assembly sealing ring 578 are used to prevent air leak from the air adjustment chamber 811 and the center hollow air passage 571.

In certain embodiments, the heating element 54 is disposed on and in direct contact with the inside wall of the e-liquid medium 55. The heating element 54 has a first terminal 541, and a second terminal 542. The first terminal 541, and the second terminal 542 of the heating element 54 are connected to a first terminal and a second terminal of an electrical power supply, respectively to receive electric power for the heating element. The vaporizer tube 53 is disposed on and in contact with the outside wall of the e-liquid medium 55. The vaporizer tube 53 has a lower end and an opposite, upper end. The vaporizer tube 53 defines a predetermined number of e-liquid conduit openings 51. These e-liquid conduit openings 51 are used to allow e-liquid from an e-liquid storage tank 7 disposed outside of the vaporizer 5 to flow into the e-liquid medium 55. In certain embodiments, the e-liquid medium 55 is made from at least one of: cotton fibers, polypropylene fibers, terylene fibers, nylon fibers; and porous ceramic materials.

When a user fills the e-liquid storage tank 7 with e-liquid, the e-liquid from the e-liquid storage tank 7 flows to the e-liquid medium 55 through the e-liquid conduit openings 51, and is vaporized by the heating element 54 when the user connects the electric power supply to the first terminal 541 and the second terminal 542 of the heating element 54. In one embodiment, the heating element has a heating wire, and the heating wire is wound in a spiral shape. In other embodiments, the heating wire may be wound in a triangular, square, polygon, or oval shapes.

Figure 9:
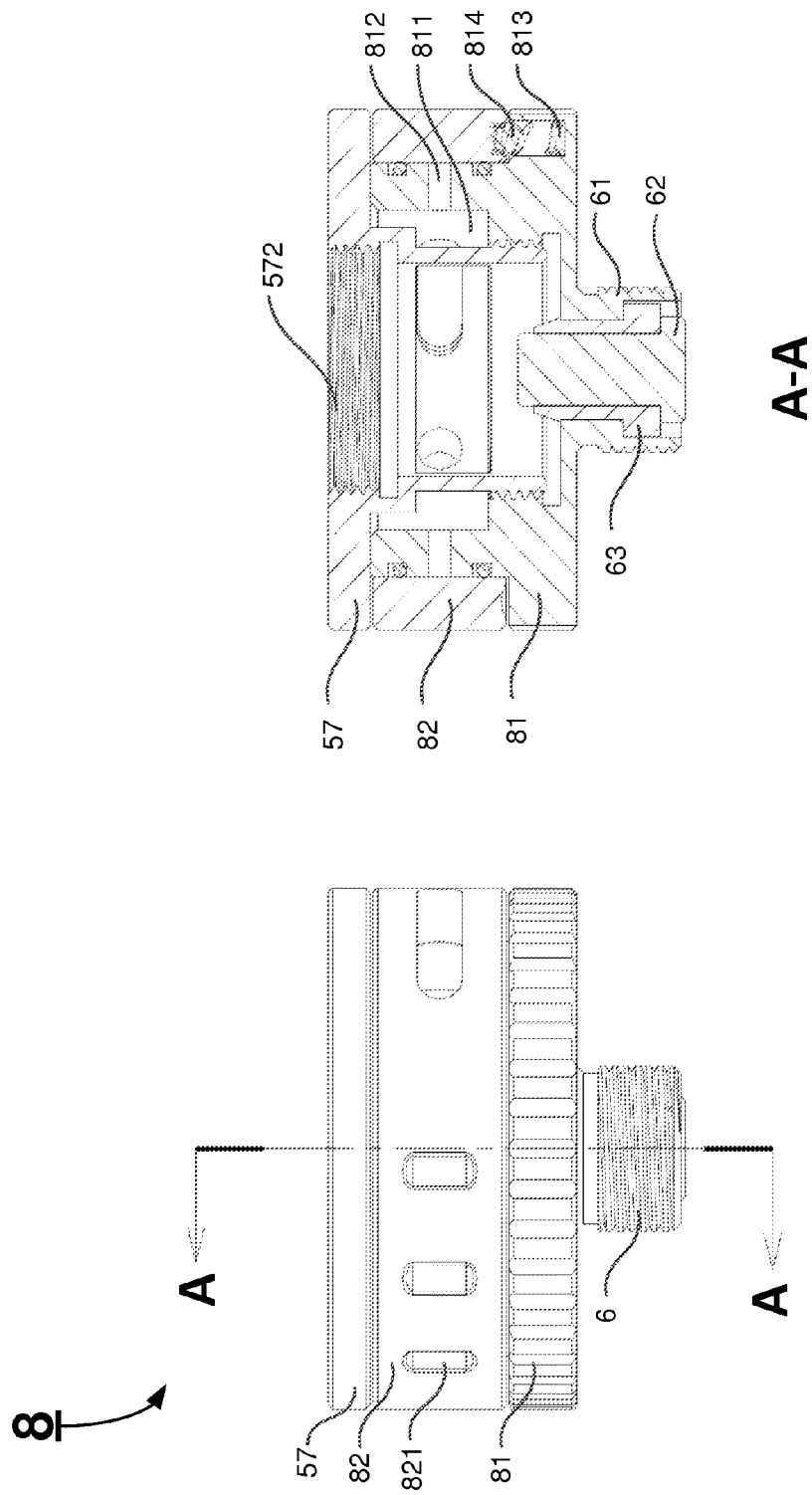
FIG. 9 is a side view and a cross-sectional view of an air adjustment assembly for the top refillable electronic cigarette according to certain embodiments of the present invention.
Figure 10:
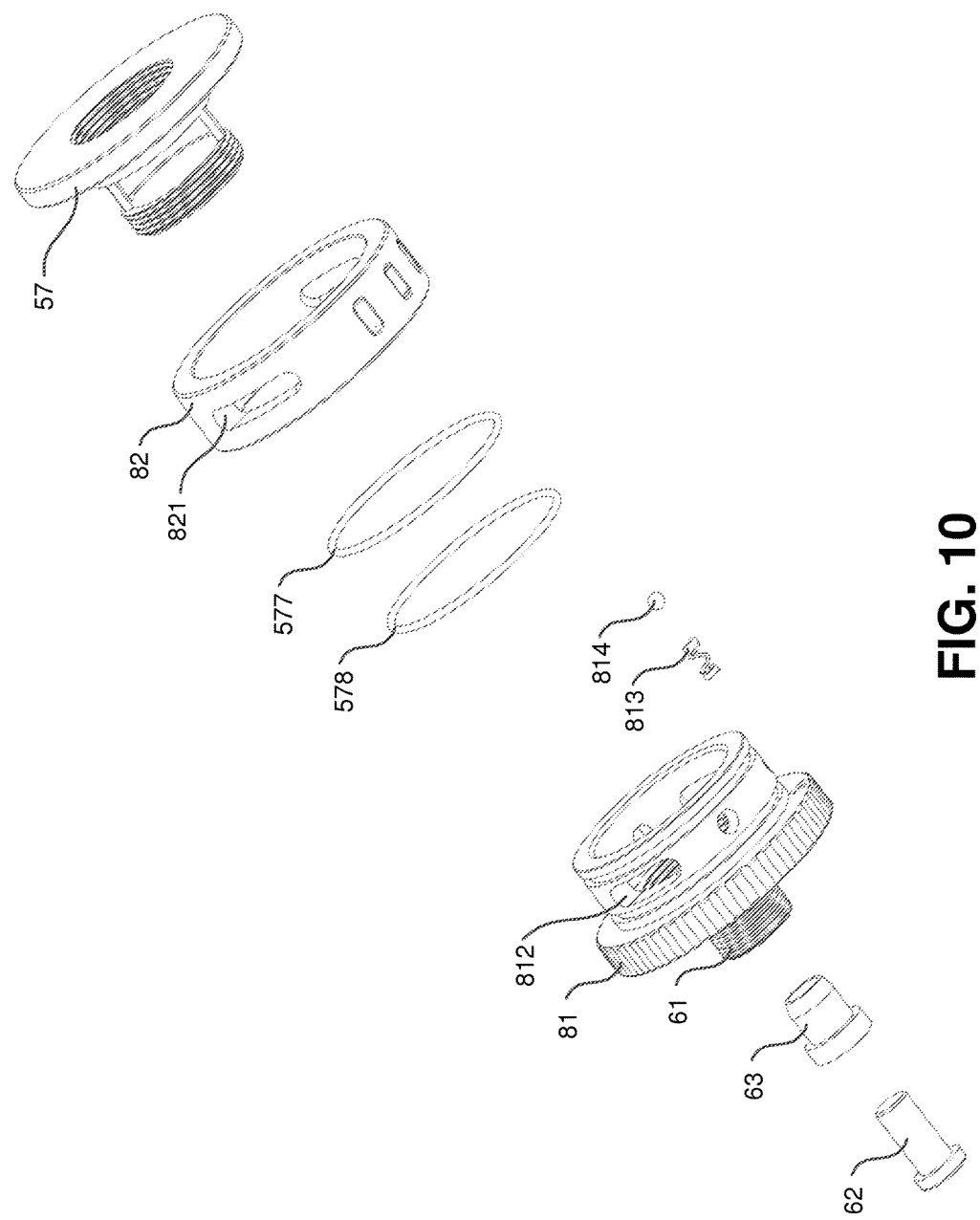
FIG. 10 is a perspective exploded view of the air adjustment assembly for the top refillable electronic cigarette according to certain embodiments of the present invention.

Referring now to FIGS. 9-10, a side view, a cross-sectional view and a perspective exploded view of the air adjustment assembly for the top refillable electronic cigarette are shown according to certain embodiments of the present invention. The air adjustment assembly 8 includes: an air adjustment assembly base 81, an air adjustment ring 82, and a sealing ring 85. The air adjustment assembly base 81 has an upper tubular portion threadedly connected to the lower outside threaded portion 561 of the lower connecting assembly 56, an air adjustment chamber 811 defined inside of the air adjustment assembly base 81, and a predetermined number of first air vents 812. The air adjustment ring 82 is positioned outside of the upper tubular portion of the air adjustment assembly base 81. The air adjustment ring 82 has a predetermined number of second air vents 821. The sealing ring 85 is used to prevent air leak from the air adjustment assembly 8. When the user rotates the air adjustment ring 82 around the upper tubular portion of the air adjustment assembly base 81, and when the locations of the second air vents 821 of the air adjustment ring 82 align with the locations of the first air vents 812, air flow from outside of the electronic cigarette to the air adjustment chamber 811 reaches maximum capacity. When the user further rotates the air adjustment ring 82 around the upper tubular portion, the air flow decreases, and when the locations of the second air vents 821 of the air adjustment ring 82 completely misalign with the locations of the first air vents 812, the air flow stops.

In certain embodiments, the air adjustment assembly 8 further includes a rotation stop spring 813, and a rotation stopper 814. The rotation stop spring 813 is positioned under the rotation stopper 814. The rotation stopper 814 is positioned under the air adjustment ring 82. When the user finishes the air adjustment rotation, the rotation stopper 814 holds the air adjustment ring 82 in place using its surface frictional force and the resilient force of the rotation stop spring 813.

When the user adjusts the air adjustment assembly 8 and sets the air flow to a preferred level, the air outside of the air adjustment assembly 8 flows into the air adjustment chamber 811. The air adjustment chamber 811 is connected to the vaporizer 5 through the center hollow air passage 571 of the circular vaporizer connector 57, and the air in the air adjustment chamber 811 flows into the e-liquid medium support 551. The e-liquid in the e-liquid medium 55 is vaporized by the heating element 54 to generate vapor with the air supplied into the e-liquid medium support 551, and provides vaporized e-liquid to the user through a mouthpiece assembly (as shown in FIGS. 1-4).

In certain embodiments, the electronic cigarette 100 further includes an electric connector assembly 6, as shown in FIG. 9. The electric connector assembly 6 has: an electric connector base 61, an electrode 62, and an insulation cover 63. The electric connector base 61 is attached to the air adjustment assembly 8 and adapted for connecting a first terminal of the electric power supply to the heating element 54 of the vaporizer 5. The electric connector base 61 has an outer thread configured to electrically connect the first terminal of the electric power supply to the first terminal 541 of the heating element 54. The electrode 62 is used to electrically connect a second terminal of the electric power supply to the second terminal 542 of the heating element 54. The insulation cover 63 is positioned between the electric connector base 61 and the electrode 62 to provide insulation between the first and the second terminals of the electric power supply. In one embodiment, the electric power supply is low voltage direct current power supply. In another embodiment, the electric power supply is a rechargeable battery. In yet another embodiments, the electric power supply is a lithium-ion rechargeable battery.

When a user fills the e-liquid storage tank 7 with e-liquid, the e-liquid from the e-liquid storage tank 7 flows to the e-liquid medium 55 through the e-liquid conduit openings 51, and is vaporized by the heating element 54 when the user connects the electric power supply to the first terminal 541 and the second terminal 542 of the heating element 54. In one embodiment, the heating element has a heating wire, and the heating wire is wound in a spiral shape. In other embodiments, the heating wire may be wound in a triangular, square, polygon, or oval shapes.

Figure 4:
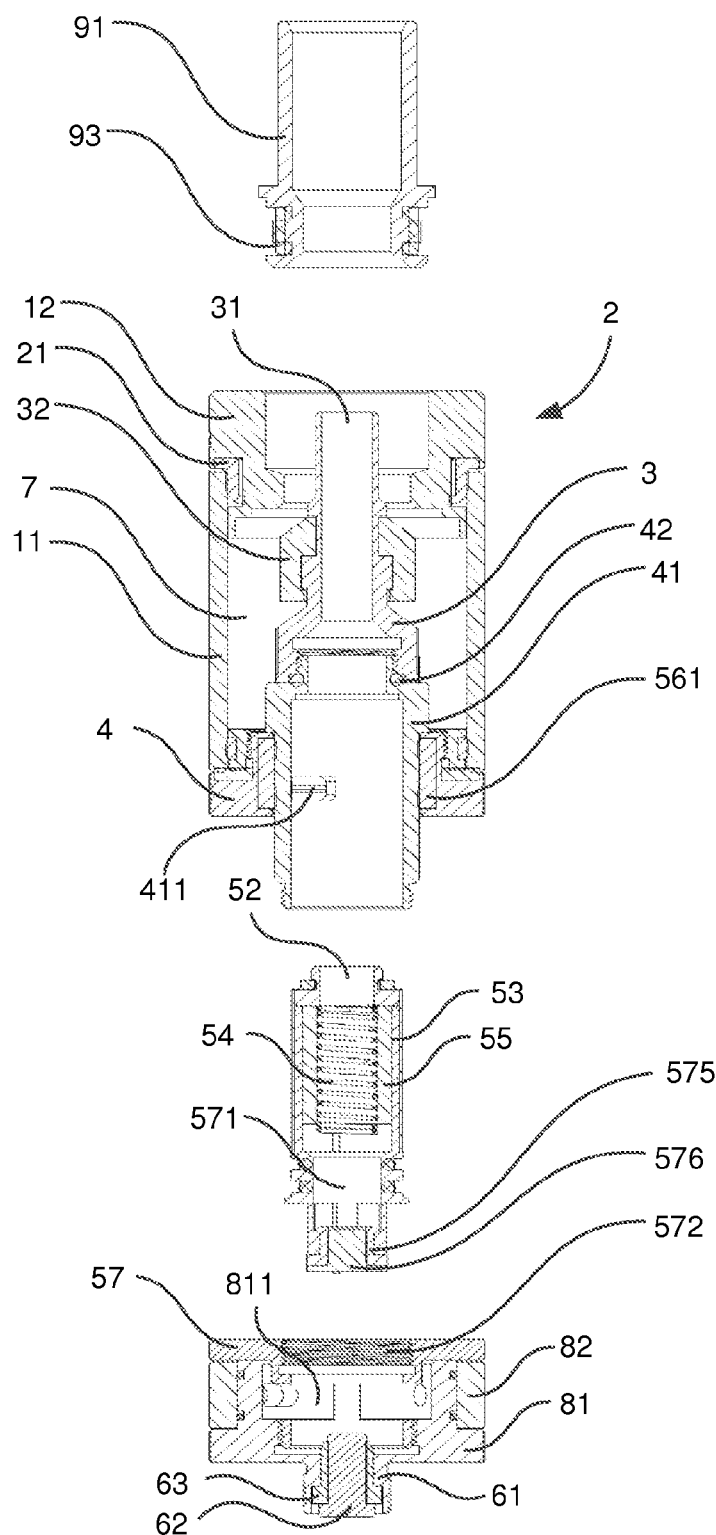
FIG. 4 is another cross-sectional view of the top refillable electronic cigarette according to certain embodiments of the present invention.

In certain embodiments, the electronic cigarette 100 further includes an e-liquid storage assembly 2. Referring now to FIG. 4, an exploded cross-sectional view of the top refillable electronic cigarette 100 illustrates the e-liquid storage assembly 2 of the top refillable electronic cigarette 100 according to certain embodiments of the present invention. The e-liquid storage assembly 2 has: an e-liquid storage top sealing ring 21, an e-liquid storage bottom sealing ring 22, a transparent e-liquid storage tube 11, and the e-liquid storage support 12. The e-liquid storage top sealing ring 21 seals the top of the e-liquid storage assembly 2. The e-liquid storage bottom sealing ring 22 seals the bottom of the e-liquid storage assembly 2. The e-liquid storage tank 7 is defined inside of the e-liquid storage assembly 2 vertically between the e-liquid storage bottom sealing ring 22 and the e-liquid storage top sealing ring 21, and horizontally between the vaporizer tube 53 and the transparent e-liquid storage tube 11. The transparent e-liquid storage tube 11 configured to allow the user to visually measure the remaining e-liquid in the e-liquid storage assembly 2. The e-liquid storage tube 11 can be made from at least one of: a glass material, a transparent ceramic material, and a crystalline material.

In certain embodiments, the e-liquid storage assembly 2 is sealed on the top by the e-liquid storage top sealing ring 21, and at the bottom by the e-liquid storage bottom sealing ring 22. The sliding base 4 has a cylindrical top portion 41 and a threaded portion 42 on the cylindrical top portion 41. The threaded portion 42 of the sliding base 4 is threadedly connected to the lower end thread of the e-liquid storage support 12. The e-liquid storage support 12 has the upper end thread configured to threadedly connect to the mouthpiece assembly 9.

Referring now to FIG. 3, the perspective exploded view of the top refillable electronic cigarette 100 illustrates the mouthpiece assembly 9 of the top refillable electronic cigarette 100 according to certain embodiments of the present invention. In certain embodiments, the mouthpiece assembly 9 has: a mouthpiece 91, a mouthpiece connector 92, and a mouthpiece sealing ring 93. The mouthpiece 91 has a hollow center air passage connected to the vapor passage 31 of the stationary top connecting assembly 3 and provides vaporized e-liquid to the user. The mouthpiece connector 92 has a threaded lower portion 921 threadedly connects to the upper end thread of the e-liquid storage support 12. The mouthpiece sealing ring 93 prevents the vaporized e-liquid from leaking through the mouthpiece connector 92.

In certain embodiments, the electronic cigarette further includes an e-liquid refill seal 32 as shown in FIG. 3. The e-liquid refill seal 32 is disposed on the stationary top connecting assembly 3 and configured to seal the e-liquid storage tank 7 when the mouthpiece connector 92 is installed, and allow the user to refill the e-liquid into the e-liquid storage tank 7 to the transparent e-liquid storage tube 11 when the mouthpiece connector 92 is removed.

In certain embodiments, the heating element has a heating wire, and the heating wire is wound in a spiral shape. The electronic cigarette also includes an electric power switch to allow the user to turn on and off the electronic cigarette. The electric power supply may be a rechargeable battery, or a disposable alkaline battery. The electric connector base 61 and the electrode 62 can also be used to connect to an external battery charger (not shown). When the user turns on the electrical power switch, the electric connector base 61 is internally connected to the first terminal 541 of the heating element 54, and the electrode 62 is connected to the second terminal 542 of the heating element 54. Once the heating element 54 is energized by the electrical power supply, the heating wire inside the vaporizer 5 vaporizes the e-liquid soaked in the e-liquid medium 55 to provide the vaporized e-liquid to the user through the mouthpiece 91.

In certain embodiments, the user may use the air adjustment assembly 8 to adjust the air flow into the air adjustment chamber 811. At the suction force of the user through the mouthpiece assembly 9, the air in the air adjustment chamber 811 flows up through the center hollow air passage 571 of the circular vaporizer connector 57 into the e-liquid medium support 551. When the user turns on the electric power supply, the air in the e-liquid medium support 551 is vaporized by the e-liquid soaked in the e-liquid medium 55, and then flow up through the vapor discharge 52 of the vaporizer 5, vapor passage 31 of the stationary top connecting assembly 3, and the mouthpiece 91 to the user.

In certain embodiments, the top refillable electronic cigarette 100 includes an electric power. This power switch allows the user to turn on and off the electronic cigarette. In certain embodiments, the top refillable electronic cigarette 100 includes an electric power adjustment device. This electric power adjustment device allows the user to adjust the electric power to control vaporization of the e-liquid.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims, the foregoing description and the exemplary embodiments described therein, and accompanying drawings.

What is claimed is:

1. A top refillable electronic cigarette comprising:
    a movable cylindrical electronic cigarette assembly having an e-liquid storage tank inside the movable cylindrical electronic cigarette assembly, an e-liquid storage support having an upper end thread configured to threadedly connect to a mouthpiece assembly, and a lower end thread configured to threadedly connect to a sliding base;
    a stationary top connecting assembly defining a vapor passage in the center of the stationary top connecting assembly configured to allow vaporized e-liquid from the vaporizer to pass through to the mouthpiece assembly;
    a vaporizer disposed inside the stationary top connecting assembly; and
    an air adjustment assembly configured to allow a user to adjust the amount of air intake to the top refillable electronic cigarette;
    wherein the movable cylindrical electronic cigarette assembly may be slid upwards to open an e-liquid refill port against the stationary top connecting assembly such that e-liquid may be refilled at the top through the e-liquid refill port.

2. The top refillable electronic cigarette of claim 1, wherein the vaporizer comprises:
    a circular vaporizer connector having an upper end, and an opposite lower end, wherein the circular vaporizer connector defines a center hollow air passage through the lower end to the upper end;
    a e-liquid medium disposed on the upper end of the circular vaporizer connector, wherein the e-liquid medium has an inside wall and an outside wall and defines a circular vaporizing chamber having a lower end connected to the center hollow air passage of the circular vaporizer connector, and an upper end forming a vapor discharge;
    a heating element disposed on and in contact with the inside wall of the e-liquid medium, wherein the heating element has a first terminal, and a second terminal; and
    a vaporizer tube disposed on and in contact with the outside wall of the e-liquid medium, wherein the vaporizer tube has a lower end and an opposite, upper end defines a plurality of e-liquid conduit openings configured to allow e-liquid from the e-liquid storage tank outside of the vaporizer to flow into the e-liquid medium,
    wherein when the user fills the e-liquid storage tank with e-liquid, the e-liquid from the e-liquid storage tank flows to the e-liquid medium through the plurality of e-liquid conduit openings, and is vaporized by the heating element when the user connects an electric power supply to the first terminal and the second terminal of the heating element.

3. The top refillable electronic cigarette of claim 2, wherein the e-liquid medium comprises:
    cotton fibers;
    polypropylene fibers;
    terylene fibers;
    nylon fibers; and
    porous ceramic materials.

4. The top refillable electronic cigarette of claim 2, wherein the vaporizer tube comprises upper end threads configured to connect to the stationary top connecting assembly, and a vaporizer tube sealing ring configured to seal the connection with the stationary top connecting assembly.

5. The top refillable electronic cigarette of claim 2, wherein the heating element comprises a heating wire wound in a spiral shape.

6. The top refillable electronic cigarette of claim 2, wherein the circular vaporizer connector comprises lower end threads configured to connect to a lower connecting assembly.

7. The top refillable electronic cigarette of claim 6, wherein the lower connecting assembly comprises an upper inside threaded portion threadedly coupled to the lower end threads of the circular vaporizer connector, and a lower outside threaded portion threadedly coupled to the air adjustment assembly.

8. The top refillable electronic cigarette of claim 1, wherein the air adjustment assembly comprises:
an air adjustment assembly base having an upper tubular portion threadedly connected to the lower outside threaded portion of the lower connecting assembly, an air adjustment chamber defined inside of the air adjustment assembly base, and a plurality of first air vents;
an air adjustment ring disposed outside of the upper tubular portion of the air adjustment assembly base, wherein the air adjustment ring comprises a plurality of second air vents; and
a sealing ring configured to prevent air leak from the air adjustment assembly,
wherein when the user rotates the air adjustment ring around the upper tubular portion of the air adjustment assembly base, and when the locations of the plurality of second air vents of the air adjustment ring match the locations of the plurality of first air vents, air flow from outside to the air adjustment chamber reaches maximum capacity, and when the user further rotates the air adjustment ring around the upper tubular portion, the air flow decreases, and when the locations of the plurality of second air vents of the air adjustment ring completely misalign with the locations of the plurality of first air vents, the air flow stops.

9. The top refillable electronic cigarette of claim 1, further comprising an electric connector assembly, wherein the electric connector assembly comprises:
an electric connector base attached to the air adjustment assembly and adapted for connecting an electric power supply to the heating element of the vaporizer, wherein the electric connector base comprises an outer thread configured to electrically connect a first terminal of the electric power supply to the first terminal of the heating element;
an electrode configured to electrically connect a second terminal of the electric power supply to the second terminal of the heating element; and
an insulation cover positioned between the electric connector base and the electrode to provide insulation between the first and the second terminals of the electric power supply.

10. The top refillable electronic cigarette of claim 1, further comprising an e-liquid storage assembly, wherein the e-liquid storage assembly comprises:
an e-liquid storage top sealing ring configured to seal the top of the e-liquid storage assembly;
an e-liquid storage bottom sealing ring configured to seal the bottom of the e-liquid storage assembly;
a transparent e-liquid storage tube configured to allow the user to measure the remaining e-liquid in the e-liquid storage assembly; and
the vaporizer body support,
wherein the e-liquid storage tank is defined inside of the e-liquid storage assembly vertically between the e-liquid storage bottom sealing ring and the e-liquid storage top sealing ring, and horizontally between the vaporizer tube and the transparent e-liquid storage tube.

11. The top refillable electronic cigarette of claim 1, wherein the mouthpiece assembly comprises:
a mouthpiece having a hollow center air passage connected to the vapor passage of the stationary top connecting assembly and configured to provide vaporized e-liquid to the user;
a mouthpiece connector having a threaded lower portion threadedly connected to the vaporizer body support; and
a mouthpiece sealing ring configured to prevent the vaporized e-liquid to leak from the mouthpiece connector.

12. The top refillable electronic cigarette of claim 1, further comprising an e-liquid refill sealing element disposed on the stationary top connecting assembly and configured to seal the e-liquid storage tank when the mouthpiece connector is installed and allow the user to refill the e-liquid into the e-liquid storage tank through the transparent e-liquid storage tube when the mouthpiece connector is removed.

13. The top refillable electronic cigarette of claim 1, further comprising an electric power switch configured to allow the user to turn on and off the top refillable electronic cigarette.

14. The top refillable electronic cigarette of claim 1, further comprising an electric power adjustment device configured to allow the user to adjust the electric power to control vaporization of the e-liquid.

* * * * *